United States Patent [19]

Lorenzi et al.

[11] Patent Number: 4,598,250

[45] Date of Patent: Jul. 1, 1986

[54] CORROSION SENSOR DEVICE INCLUDING SIDE-BY-SIDE BAR MAGNETS SURROUNDED BY A COIL

[75] Inventors: Donald E. Lorenzi; Helmut F. Wagerer, both of Des Plaines, Ill.

[73] Assignee: Magnaflux Pipeline Services, Inc., Stamford, Conn.

[21] Appl. No.: 350,401

[22] Filed: Feb. 19, 1982

[51] Int. Cl.⁴ .................... G01N 27/72; G01R 33/12; G01D 9/00
[52] U.S. Cl. .................... 324/220; 324/226; 324/240; 346/33 P
[58] Field of Search ............... 324/226, 260, 239–243, 324/219–221, 225, 174; 346/33 P, 107 W; 354/63; 336/30, 110

[56] References Cited

U.S. PATENT DOCUMENTS

| | | | |
|---|---|---|---|
| 2,897,438 | 7/1959 | Fearon | 324/221 |
| 3,315,154 | 4/1967 | Nattall | 324/232 |
| 3,449,662 | 6/1969 | Wood | 324/220 |
| 4,314,202 | 2/1982 | Okubo | 324/207 |
| 4,372,658 | 2/1983 | O'Connor et al. | 346/33 P |

*Primary Examiner*—Ernest F. Karlsen
*Assistant Examiner*—Walter E. Snow
*Attorney, Agent, or Firm*—Neuman, Williams, Anderson & Olson

[57] ABSTRACT

A corrosion probe is disclosed which includes two permanent bar magnets in side-by-side relation, with opposite magnetic orientation and with poles of opposite polarity adjacent a sensing end of the probe, a sensing coil being disposed around the magnets adjacent the sensing end. The probe is disclosed in use in a pipe inspection pig for controlling operation of a camera.

6 Claims, 5 Drawing Figures

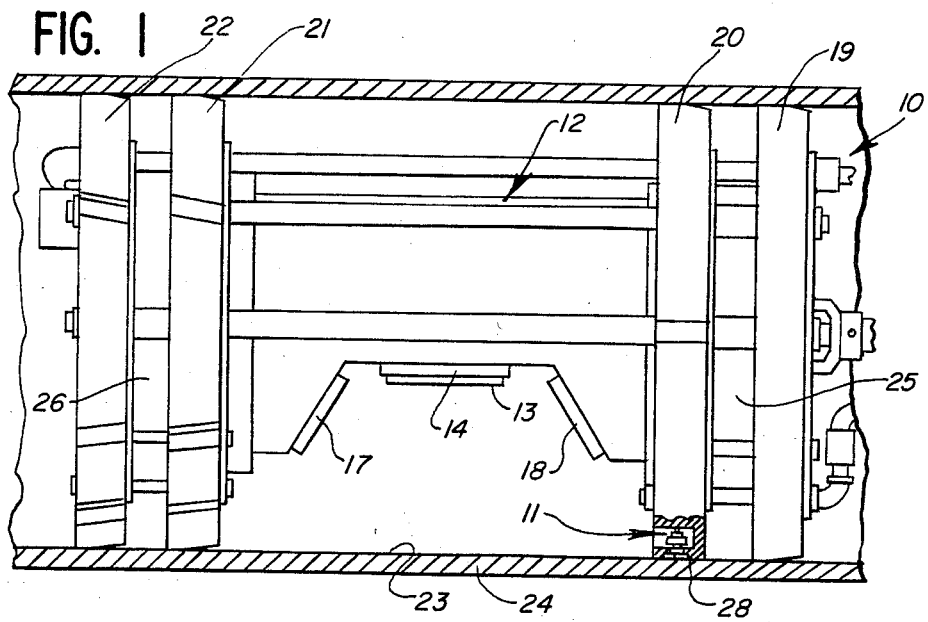
FIG. 1
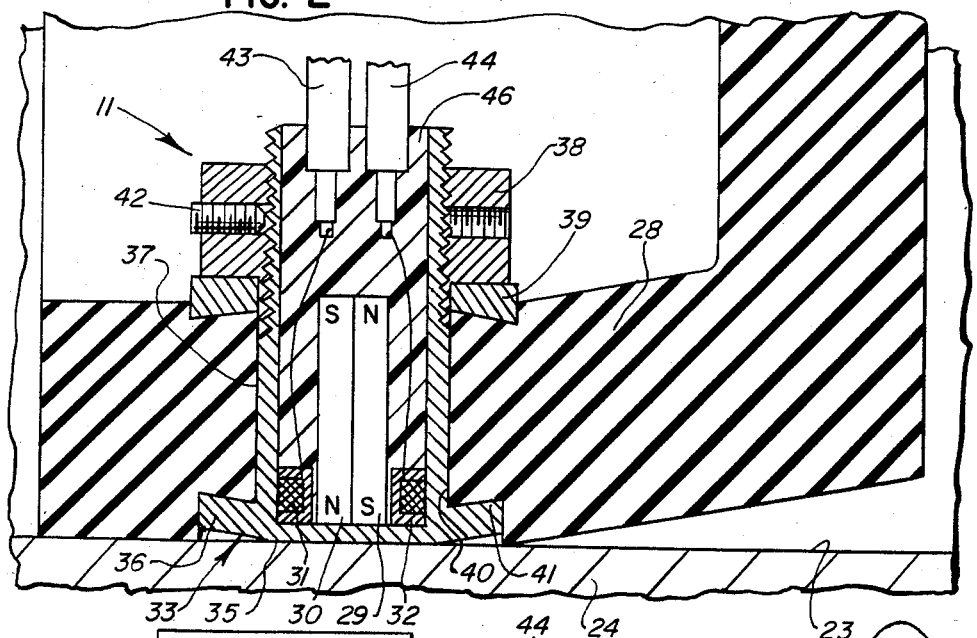
FIG. 2
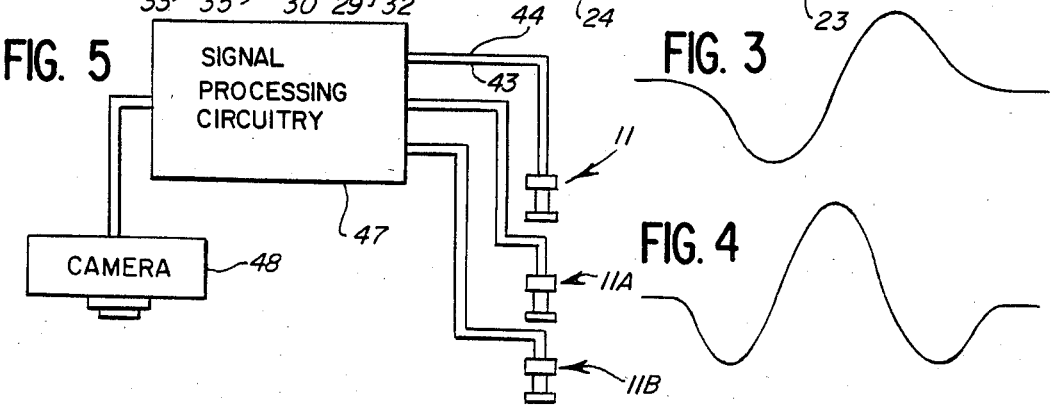
FIG. 5
FIG. 3
FIG. 4

CORROSION SENSOR DEVICE INCLUDING SIDE-BY-SIDE BAR MAGNETS SURROUNDED BY A COIL

This invention relates to a corrosion sensor device and more particularly to a device which is arranged to detect corrosion pits or the like. The device of the invention is very sensitive and is highly reliable while being quite simple in construction and operation and readily and economically manufacturable. It is particularly advantageous in use in a photographic pipe inspection pig structure.

BACKGROUND OF THE INVENTION

Devices have heretofore been provided which are capable of detecting corrosion pits or the like but such devices have generally been insensitive to pits to be detected, especially when the device is located at a substantial spacing distance from a surface in which the pits are to be detected. The prior art devices have also been relatively expensive to construct and they have not been suitable for use in many applications. A particular problem relates to the detection of pits or the like with a moving probe device and especially when there may be a variation in spacing between the probe and the surface in which the pits are to be detected.

SUMMARY OF THE INVENTION

This invention was evolved with the general object of overcoming disadvantages of prior art devices and providing a device which is highly sensitive to corrosion pits or the like while being rugged and reliable in operation.

A specific object of the invention is to provide a device suitable for pipe inspection to detect corrosion pits which can cause serious problems if remedial operations are not performed.

In a device constructed in accordance with the invention, a pair of magnets are provided, each of which may preferably be in the form of a permanently magnetized elongated bar. Such magnets are disposed in side-by-side relation but with an opposite orientation of the poles, a north pole on one magnet being positioned at a sensing end of the device while a south pole of the other magnet is positioned at the sensing end of the device. Means are provided for detecting differences with respect to the fields of the magnets, preferably including coil means around the magnets and most preferably, a single coil is provided extending around the two bar magnets.

With this very simple arrangement, a high degree of sensitivity can be obtained in the detection of corrosion pits. Preferably, the relative magnetic fields respectively produced when the poles of the magnets are positioned over a pit are compared which may be conveniently accomplished by moving the probe in a direction to sequentially position the poles of the two magnets over a pit while measuring the rate of change of the difference between the fields produced by the magnets.

An important advantage of the device is that it can be highly insensitive to changes in spacing between the sensing end of the probe and a surface in which pits are to be detected.

Additional important features of the invention relate to the use of the probe in a pig device which is used for inspection of the inside of a pipe. One of such features relates to the mounting of the probe in the peripheral wall of a resilient cup member which engages the inside of the pipe and which supports the pig device. The mounting of the probe is readily accomplished and when mounted in the periphery of a cup, it is held in contact with the inside surface of the pipe to obtain highly accurate and reliable results. Preferably, the pig is so weighted as to be pulled by gravity into a certain angular orientation when moved in a horizontal pipe run and the probe is positioned on the lower side of the device. This is advantageous because it is found that corrosion pits are most likely to occur on the lower inside upwardly facing surface of the pipe which is most likely to be exposed to moisture.

Another feature relates to the combination of the device with photographic camera means in an inspection pig. Corrosion pits can be accurately detected with the device of the invention but it is desirable to be able to verify the results obtained and a photographic picture is highly desirable in this respect. A photographic picture is also highly advantageous in that it can show a large surface area of the pipe, to readily determine the extent of any corrosion. Properly constructed, a photographic inspection device is highly advantageous for this reason and others but it does have one limitation in that photographing the entire length of a long pipe run would require exposure, developing and analysis of an extremely long length of film. In accordance with the invention, a magnetic sensing probe, presently the probe of the invention, is provided for detection of corrosion pits and to develop a signal which is processed and used to control operation of the camera. In this way, the amount of film which must be exposed, developed and analyzed is greatly reduced and a photographic inspection device is obtained which can be used in very long lengths of pipeline.

This invention contemplates other objects, features and advantages which will become more fully apparent from the following detailed description taken in conjunction with the accompanying drawings.

BRIEF DESCRIPTION OF THE DRAWINGS

FIG. 1 is a side elevational view of a pipeline inspection device constructed in accordance with the invention, shown in position in a pipe, a portion of a cup element of the device being cut away to show the position of mounting of a corrosion sensor device, according to the invention;

FIG. 2 is an elevational sectional view on a greatly enlarged scale with respect to FIG. 1, showing the construction of the corrosion sensor device;

FIG. 3 graphically depicts the way in which the field through a sensing coil of the device changes with time as the device moves over a corrosion pit;

FIG. 4 graphically depicts the way in which the induced voltage in the sensing coil changes with time as the device moves over a corrosion pit; and FIG. 5 is a schematic diagram illustrating the use of the corrosion sensor device in controlling operation of a camera of the pipeline inspection device.

DESCRIPTION OF A PREFERRED EMBODIMENT

Reference numeral 10 generally designates a photographic pipeline inspection device which incorporates a corrosion sensing device generally designated by reference numeral 11. The device 10 is designed to be launched into a pipeline used for transport of natural gas and to be moved through the pipeline by the pressure of the gas. The illustrated device is designed to be pulled through the pipeline by a tow pig in front of the device but it could be designed to be moved itself by the pressure of the gas. While the device 10 travels through the pipeline, photographs are taken of the internal surface of the pipe by a camera which is disclosed within a housing 12 and above a protective glass plate 13 which is held by a support 14 on a horizontal wall portion 15 of the housing 12. The surface of the pipe is illuminated by one or two strobe lights which may be disposed behind a pair of ports 17 and 18 on inclined wall portions of the housing 12, the ports 17 and 18 having glass windows for transmission of light therethrough.

The housing 12 is supported between two forward cups 19 and 20 and two rearward cups 21 and 22, the cups 19 and 22 being of a resilient elastomeric material and having annular peripheral flange portions for sliding engagement with the inside surface 23 of a pipe 24 in which the device is moved. Spacing structures 25 and 26 are provided between the cups 19 and 20 and between the cups 21 and 22 and one or both of such structures carries weight means operative to place the device in the angular orientation as shown, such that photographs are taken of the lower inside upwardly facing surface area of a horizontal pipe.

It will be understood that the device 10 may have a number of additional features, including means for clearing the exposed surface of the plate 13 and means for controlling the atmospheric conditions within the space between the camera and the surface of the pipe.

As shown in FIG. 1, the sensor device 11 is mounted in a peripheral portion 28 of the cup 20 and at a "6:00 o'clock" position such as to engage the lowermost portion of the inside surface of the pipe 24.

FIG. 2 shows the construction of the probe device 11. A pair of magnets 29 and 30 are provided, each of which is preferably a permanently magnetized bar magnet and, by way of example, two Alnico magnets may be used, each being a ⅛ inch X X ⅛ inch X ¾ inch magnet. As shown, the magnets are disposed in side-by-side parallel relation with the south pole of the magnet 29 and the north pole of the magnet 30 at the lower end of the probe 11.

A coil 31 is wound on a bobbin 32 and is disposed around the lower ends of the magnets 29 and 30 within a housing 33 which includes a lower end wall 34, the exposed lower surface of which is engageable with the surface of the pipe 24, forming a wear face 35. Preferably, the peripheral edge portions of the face may be beveled as shown to allow the device to ride over projections in the pipe surface.

For mounting of the device in the flange portion 28 of the cup 20, the housing 33 is formed with a lower larger diameter flange portion 36 and an upper smaller diameter hollow cylindrical portion 37, at least the upper portion of which is externally threaded to receive a jam nut 38, a washer 39 being disposed on the portion 37 for engagement with the upper side of the flange portion 28 of the cup 20. To mount the device, a hole 40 is formed in the flange portion 28 for receiving the portion 37 of the housing while a counter bore 41 may be formed for receiving the flange portion 36. After extending the portion 37 through the hole 40, the washer 39 and then the nut 38 are installed, the nut being tightened. Then a set screw 42 may be installed in one of a plurality of holes in the nut 38, a plurality of holes being provided to insure that at least one will be accessible.

The ends of the coil are extended and connected to the ends of the conductors of a pair of insulated lead wires 43 and 44. A suitable potting compound 46 may be used to hold the wires and components in place and to protect the same.

The housing 33 is preferably of stainless steel and at least the end wall 34 is non-magnetic. If desired, a separate part may be used to form the end wall 34 and to provide the wear face 35.

The sensor operates as a leakage flux device. On a smooth surface, the magnetic flux through the coil 31 is constant and no voltage is induced in the coil. Moreover, if the magnets have the same strength, there is no net magnetic flux through the coil 31 and it is found that the device is insensitive to changes in spacing between the ends of the magnets 29 and 30 and the surface of the pipe 24 or other part inspected. The device may be sensitive to tilting movement but with a mounting as shown, it can be maintained in the proper angular position.

When the sensor 11 in moving from left to right with reference to FIG. 2, moves over a corrosion pit, the magnetic field through the coil 31 will decrease as the magnet 29 moves over the pit and will then increase as the magnet 30 moves over the pit, to produce a field variation with time as depicted graphically in FIG. 3. The corresponding voltage induced in the coil will be as depicted in FIG. 4, reaching a maximum at the point where the rate of change of the field is the greatest. It is found that the device is thus highly sensitive to corrosion pits while being insensitive to normal variations in the spacing between the sensing end of the probe and the metallic surface of the pipe 24 or other parts being inspected.

As diagrammatically shown in FIG. 5, the device is connected to signal processing circuitry 47 which is connected to a camera 48 disposed within the housing 12 to take pictures through the window formed by the glass plate 13. The processing circuitry includes a threshold detector operative to develop a signal only when the sensor output signal exceeds a certain threshold level and it also includes delay and output circuits operative to apply a signal to the camera 48 to cause the camera to take a picture of areas in which corrosion pits are detected. As also illustrated diagrammatically in FIG. 5, the processing circuitry 47 may be connected to additional corrosion sensor probes 11A and 11B which may, for example, be mounted in the flange portion 28 in angular spaced relation to the device 11 but in the lower portion of the flange 28. By providing a plurality of probes, a more reliable detection of corrosion may be obtained. It is also noted that the processing circuitry may include means for storing signals and for producing a camera-operating signal after detection of a certain number of corrosion pits within a certain distance of travel of the device.

It will be understood that modifications and variations may be effected without departing from the spirit and scope of the novel concepts of this invention.

We claim:

1. A sensor device, comprising: a probe having a sensing end which during use of the probe is positioned adjacent a surface of a part for detection of corrosion pits or the like, first and second elongated bar magnets positioned in said probe in fixed closely adjacent parallel relation to each other and with the north pole of said first magnet and the south pole of said second magnet adjacent each other at said sensing end of said probe and with the south pole of said first magnet and the north pole of said second magnet spaced from said sensing end, and detector means including a coil and circuit means for responding to the magnetic field through said coil, said coil being wound around said first and second elongated bar magnets in stationary relation thereto with all turns of said coil being in encircling relation to both magnets and with the net magnetic field through said coil being equal to the difference of the fields of said first and second magnets, the fields of said magnets being substantially the same when said sensing end of said probe is positioned opposite and at varying distances from a part surface portion which is free of corrosion pits, the field of said first magnet being reduced when said north pole thereof is positioned adjacent a corrosion pit while said south pole of said second magnet is opposite a part surface portion which is free of corrosion pits and to then produce a net field through said coil in one direction, and the field through said second magnet being reduced when said south pole thereof is positioned opposite a corrosion pit while said north pole of said first magnet is positioned opposite a part surface portion which is free of corrosion pits and to then produce a net field through said coil in the opposite direction.

2. In a sensor device as defined in claim 1, each of said bar magnets being a permanent magent of generally square cross-sectional shape with one side surface of said first magnet being engaged with one side surface of said second magnet, and said magnets having substantially the same length.

3. In a sensor device as defined in claim 2, the width of each of said bar magnets being on the order of ⅛ inch.

4. In apparatus for use in pipe inspection, a probe having a sensing end which during use of the probe is positioned adjacent a surface of a part for detection of corrosion pits or the like, first and second elongated bar magnets positioned in said probe in fixed closely adjacent parallel relation to each other and with the north pole of said first magnet and the south pole of second magnet adjacent each other at said sensing end of said probe and with the south pole of said first magnet and the north pole of said second magnet spaced from said sensing end, detector means including a coil and circuit means for responding to the magnetic field through said coil, said coil being wound around said first and second elongated bar magnets in stationary relation thereto with all turns of said coil being in encircling relation to both magnets and with the net magnetic field through said coil being equal to the difference of the fields of said first and second magnets, the fields of said magnets being substantially the same when said sensing end of said probe is positioned opposite and at varying distances from a part surface portion which is free of corrosion pits, the field of said first magnet being reduced when said north pole thereof is positioned adjacent a corrosion pit while said south pole of said second magnet is opposite a part surface portion which is free of corrosion pits and to then produce a net field through said coil in one direction, and the fireld through said second magnet being reduced when said south pole thereof is positioned opposite a corrosion pit while said north pole of said first magnet is positioned opposite a part surface portion which is free of corrosion pits and to then produce a net field through said coil in the opposite direction and support means for supporting said probe for longitudinal movement within a pipe while maintaining said sensing end of said probe in proximity to the internal surface of the pipe and while positioning the longitudinal axes of said bar magnets in transverse relation to the longitudinal axis of the pipe, the longitudinal axes of said magnets being spaced in a direction parallel to the longitudinal axis of the pipe with the field through said coil when passing over a corrosion pit having a maxixum rate of change in one direction when the corrosion pit is midway between the longitudinal axes of said magnets.

5. In apparatus as defined in claim 4, said probe including a wall having one surface engaged with said north and south poles of said first and second magnets and having an opposite surface defining a wear face for sliding engagement with the internal surface of the pipe.

6. In apparatus as defined in claim 5, said support means comprising a pig which includes a plurality of cup means having peripheral flange portions in engagement with longitudinally space internal surface portions of the pipe, said probe being mounted in a flange portion of one of said cup means, photographic camera means carried by said pig and controlled by said circuit means to photograph the inside surface of a pipe in which pits are detected be said sensor device, said pig being weighted to position said probe to engage the lower inside surface of a horizontal pipe and to position said camera means to photograph the lower inside surface of a horizontal pipe in which pits are detected by said sensor device.

* * * * *